United States Patent [19]
Li et al.

[11] Patent Number: 5,879,295
[45] Date of Patent: Mar. 9, 1999

[54] ENHANCED CONTACT STEERABLE BOWING ELECTRODE CATHETER ASSEMBLY

[75] Inventors: Hong Li, Cupertino; Mark A. MaGuire, San Jose, both of Calif.

[73] Assignee: Medtronic, Inc., Minneapolis, Minn.

[21] Appl. No.: 825,778

[22] Filed: Apr. 2, 1997

[51] Int. Cl.⁶ .................................................. A61N 1/05
[52] U.S. Cl. .......................................... 600/373; 607/125
[58] Field of Search .................................. 607/125, 122; 600/373

[56] References Cited

U.S. PATENT DOCUMENTS

| | | |
|---|---|---|
| 5,431,696 | 7/1995 | Atlee, III . |
| 5,636,634 | 6/1997 | Kordis et al. . |
| 5,674,274 | 10/1997 | Morgan et al. . |
| 5,687,723 | 11/1997 | Avitall . |

*Primary Examiner*—Scott M. Getzow
*Attorney, Agent, or Firm*—Townsend and Townsend and Crew LLP

[57] ABSTRACT

A catheter assembly (2) includes a proximal end assembly (4), with four slidable movable manipulators (12, 14, 16, 18) and a bowing catheter (6) extending from the proximal end assembly. The bowing catheter includes an elongate, flexible catheter body (24), having a tip portion (30) carrying electrodes (32), first and second elongate push/pull manipulator wires (26, 28), and a sheath (22) housing the catheter body and manipulator wires. The sheath, catheter body and manipulator wires are each coupled to a manipulator. The manipulator wires are connected to positions (40, 42) on either side of a stiff tip segment (43). The manipulator wires have sufficient columnar strength/stiffness to maintain the tip segment at a range of relatively stable orientations to cause the bowed tip to be deflected in in-plane and out-of-plane deflections.

48 Claims, 10 Drawing Sheets

ENHANCED CONTACT STEERABLE BOWING ELECTRODE CATHETER ASSEMBLY

BACKGROUND OF THE INVENTION

The present invention relates generally to systems and methods for applying electrical energy to a patient and more specifically to steerable electrophysiology catheters for use in mapping and/or ablation of the heart.

The heart is primarily composed of multiple fibers which are responsible for the propagation of signals necessary for normal electrical and mechanical function. The presence of an arrhythmogenic site or abnormal pathway which may bypass or short circuit the normal conducting fibers in the heart often causes abnormally rapid rhythms of the heart, which are referred to as tachycardias. Tachycardias may be defined as ventricular tachycardias (VTs) and supraventricular tachycardias (SVTs). VTs originate in the left or right ventricle and are typically caused by arrhythmogenic sites associated with ventricular myocardial disease. SVTs originate in the atria or the atrioventricular (AV) junction and are frequently caused by abnormal circuits or foci.

The present invention is concerned with the treatment of atrial fibrillation and atrial flutter, which are two of the most common sustained cardiac arrhythmias and the major causes of systemic embolism. Therapy for patients suffering from atrial fibrillation usually focuses on controlling the symptoms (palpitations, angina, dyspnea, syncope and the like), improving cardiac performance and reducing the risk of thromboembolism. Treatment of atrial fibrillation may be accomplished by a variety of approaches, including drugs, surgery, implantable pacemakers/defibrillators, and catheter ablation. While antiarrhythmic drugs may be the treatment of choice for many patients, these drugs may only mask the symptoms and do not cure the underlying cause. Implantable devices, on the other hand, usually can correct an arrhythmia only after it occurs. Surgical and catheter-based treatments, by contrast, may actually cure the problem usually by ablating the abnormal arrhythmogenic tissue or abnormal pathway responsible for the atrial fibrillation or flutter. The catheter-based treatments rely on the application of various destructive energy sources to the target tissue including direct current electrical energy, radiofrequency electrical energy, microwave energy laser energy, cryoenergy, ultrasound and the like.

Of particular interest to the present invention are radiofrequency (RF) ablation protocols which have proven to be effective in treatment of atrial fibrillation while exposing the patient to minimum side effects and risks. Radiofrequency catheter ablation may be performed after an initial mapping procedure where the locations of the arrhythmogenic sites and abnormal pathways are determined. A catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the abnormal pathway. By successfully destroying that tissue, the abnormal conducting patterns responsible for the atrial fibrillation or flutter cannot be sustained. Methods and systems for performing RF ablation by controlling temperature at the ablation site are described in U.S. Pat. No. 5,573,533, issued Nov. 12, 1996, entitled "Method and System for Radiofrequency Ablation of Cardiac Tissue."

Catheters designed for mapping and/or ablation frequently include a number of individual electrode bands mounted to the distal tip of the catheter so as to facilitate mapping of a wider area in less time, or to improve access to target sites for ablation. Such catheters are described in U.S. Pat. No. 5,318,525, issued Jun. 7, 1994, entitled "Steerable Electrode Catheter." Catheters used in radiofrequency ablation are typically inserted into a major vein or artery, usually in the neck or groin area, and guided into the chambers of the heart by appropriate manipulation through the vein or artery. Such catheters must facilitate manipulation of the distal tip or ablation segment so that the distal electrode(s) can be positioned against the tissue region to be ablated. The catheter must have a great deal of flexibility to follow the pathway of the major blood vessels into the heart, and the catheter must permit user manipulation of the distal ablation segment even when the catheter is in a curved and twisted configuration. Because of the high degree of precision required for proper positioning of the tip electrode, the catheter must allow manipulation with a high degree of sensitivity and controllability.

An important factor which has driven the recent development of curative catheter ablation therapies for atrial fibrillation has been the development of a successful surgical procedure, the "Maze" procedure, for treating patients with this arrhythmia. The Maze procedure was developed to provide both sinus node control of ventricular rate and effective, appropriately synchronized biatrial contraction. This procedure involves opening the patient's chest cavity with a gross thoracotomy, usually in the form of a median sternotomy, to gain access into the patient's thoracic cavity, and cutting long linear incisions through the heart wall to electrically partition portions of the heart. In particular, the Maze procedure partitions the atria such that: (1) no portion of the atrium is large enough to support atrial fibrillation; (2) conduction of the sinus impulse to the AV node and to most portions of the atria is maintained; and (3) relatively normal atrial contraction is restored.

The success of the Maze procedure has driven interest in the development of a catheter ablation procedure which can replicate the therapeutic results of the surgical Maze procedure. This catheter ablation procedure involves the creation of relatively long linear lesions along the heart tissue with the distal tip of an ablation catheter. This desire to produce linear lesions has led to catheter designs in which several ablation electrodes are mounted on the length of the distal ablation segment of the catheter shaft.

Three requirements are important for the proper operation of electrode catheters, in particular radio frequency ablation catheters used to treat atrial fibrillation: (a) good contact between the electrodes and the heart tissue; (b) the tip portion steerable to different angles and locations; (c) easy and safe to use and easy to build. Conventional RF ablation catheters for a trial fibrillation treatment can meet some but not all of these three requirements.

A first type of linear lesion catheter has a steerable, flexible tip portion. See U.S. patent application Ser. No. 08/613,298, filed Mar. 11, 1996, entitled "Method and Apparatus for RF Ablation." While it is relatively easy to build and provides considerable maneuverability, this design does not provide for enhanced contact pressure between the electrodes along the tip portion and the heart tissue.

A second type of linear catheter carries electrodes on outwardly bowed segments at the tip portion of the catheter. See U.S. Pat. No. 5,263,493, issued Nov. 23, 1993, entitled "Deflectable Loop Electrode Array Mapping and Ablation Catheter for Cardiac Chambers." This type of catheter is generally designed to bow the electrode segment in the same plane as the catheter shaft, although it can be bowed out of plane with some effort. The primary problems with this second type are ease of maneuverability of the electrode segment into a variety of orientations, and achieving a stable position with the electrode segment.

What is needed to resolve these problems is a catheter which combines bowing out of the electrode-carrying catheter tip portion for enhanced contact with the maneuverability for out-of-plane orientations of a steerable tip design. Furthermore, the catheter should be able to make fine adjustments in the position of the tip portion, and to stabilize the tip portion in a variety of orientations. The invention described below achieves these objectives.

SUMMARY OF THE INVENTION

The present invention is directed to an enhanced contact, steerable, bowing electrode-catheter assembly in which the bowed tip portion of the catheter body can be deflected in a wide variety of directions and configurations. The stability of the bowed tip portion permits exertion of superior levels of contact force in a wide variety of directions, configurations and locations.

The catheter assembly comprises broadly a proximal end assembly, including movable manipulators, and a bowing catheter extending from the proximal end assembly. The bowing catheter includes an elongate, flexible catheter body having a tip portion carrying the electrodes. First, proximal and second, distal elongate push/pull manipulator elements are preferably coupled to first and second manipulators. The distal ends of the manipulator elements are connected to first and second spaced-apart positions at either end of a tip segment along the tip portion of the catheter body. The first and second manipulator elements have sufficient columnar strength/stiffness to position the tip segment over a range of orientations to create a radially deflected bowed tip portion. The catheter body and the manipulator elements are preferably housed within a hollow sheath. During use, a radially deflected bow is formed in the tip portion. The bowed tip portion is formed, shaped and oriented by manipulating one or more of the catheter shaft, the hollow sheath and the manipulator elements. The position, size, shape and orientation of the bowed tip portion are selected according to the lesion to be created.

In a preferred embodiment, the manipulator elements are manipulator wires which, together with the catheter body, extend through the hollow sheath. Preferably, the catheter body and the hollow sheath are connected to third and fourth manipulators. The catheter assembly preferably includes a housing to which the manipulators are movably mounted.

The tip portion is preferably introduced into the body cavity with the tip portion and manipulator elements fully housed within the sheath. When in position, the tip portion of the catheter body is extended from the distal end of the sheath. By separately or simultaneously manipulating the manipulators coupled to the manipulator wires, the catheter body and the sheath, the tip portion can be deflected to a wide variety of shapes, sizes, orientations and configurations.

The tip segment is preferably relatively rigid. The two manipulator wires and the segment tip effectively create a triangular linkage or truss structure to stabilize the tip portion. This configuration promotes good contact force between the tip portion electrodes and the organ surface.

In addition, the stability provided by truss structural arrangement helps to keep the bowed tip portion from changing shape when the entire tip portion is torqued.

(Torque-type lateral deflection is considered in-plane when the bowed tip portion does not change shape when torqued. Torque-type lateral deflection is considered out-of-plane when the bowed tip changes shape when torqued.)

Other features and advantages of the invention will appear from the following description in which the preferred embodiments have been set forth in detail in conjunction with the accompanying drawings.

DESCRIPTION OF THE PREFERRED EMBODIMENTS

Figure 1:
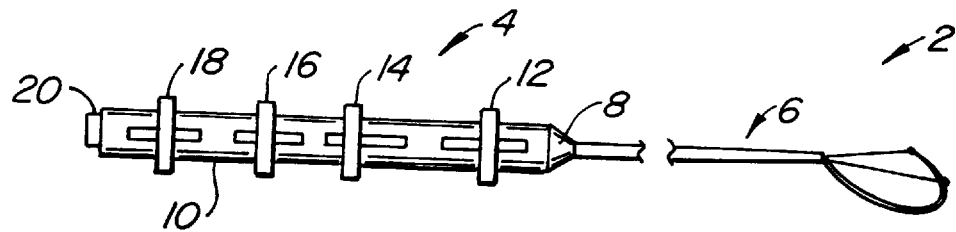
FIG. 1 is a simplified overall view of a enhanced contact steerable bowing electrode catheter assembly made according to the invention.

FIG. 1 illustrates, in simplified form, an enhanced contact steerable bowing electrode-catheter assembly 2 comprising broadly a proximal end assembly 4 and a catheter 6 extending from a distal end 8 of proximal end assembly 4. Proximal end assembly 4 includes a handle housing 10 to which four manipulators 12, 14, 16 and 18 are slidably mounted. Manipulators 12–18 are each movable along the length of housing 10 and can be secured in position by, for example, rotating the manipulator. An example of such a sliding, position-lockable manipulator is illustrated in U.S. Pat. No.

5,545,200. This permits the user to easily position one or more of the manipulators 12–18 along the longitudinal length of housing 10 and then retain the manipulator in the desired position by simply rotating the manipulator. Other means for securing manipulators 12–18 in the desired longitudinal position, such as through the use of detents or spring latches, can be used. The proximal end assembly 14 also includes an electrical connector 20 at the proximal end.

Figure 2:
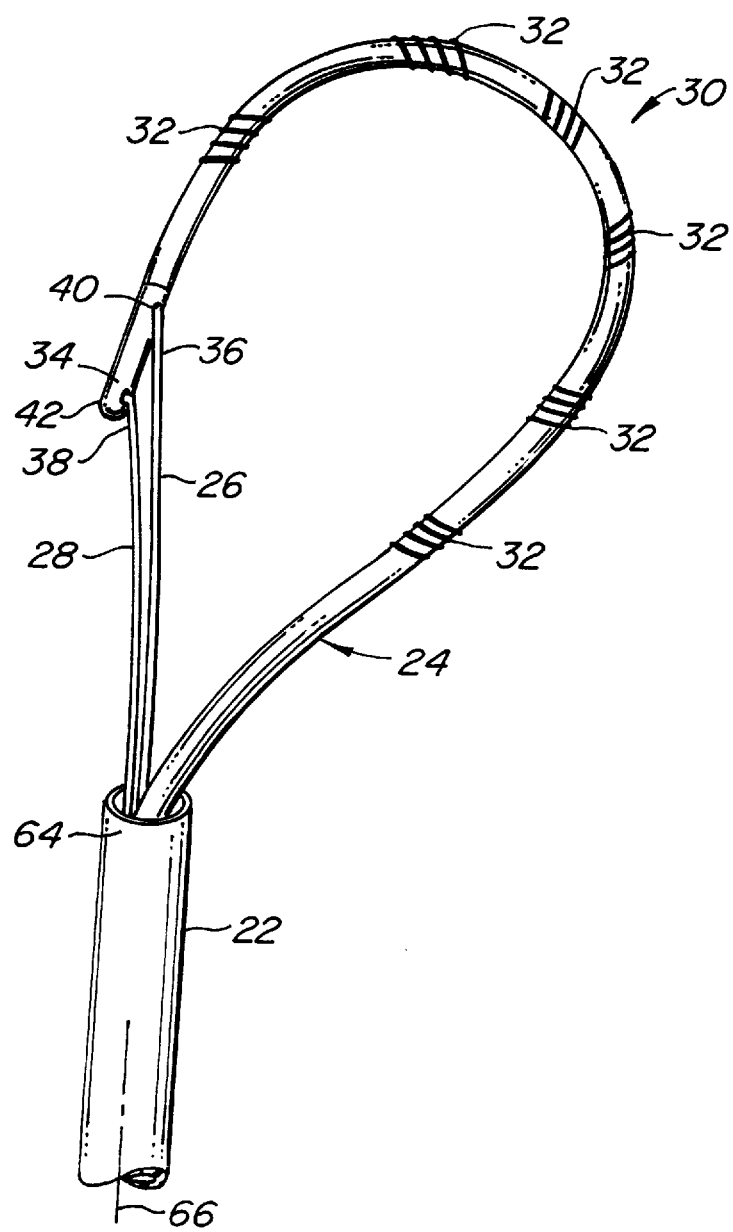
FIG. 2 is an enlarged view of the distal portion of the catheter of FIG. 1 showing the radially outwardly bowed tip portion of the catheter body extending from the sheath, the bowed tip portion lying substantially in a plane.

Referring now also to FIG. 2, catheter 6 is seen to include a hollow sheath 22 housing a catheter body 24, a first, proximal manipulator wire 26 and a second, distal manipulator wire 28. Catheter body 24 includes a tip portion 30 to which a number of electrophysiology electrodes 32 are mounted. Electrodes 32 are preferably coil electrodes to ensure good flexibility of tip portion 10.

The distal ends 36, 38 of manipulator wires 26, 28 are coupled to tip portion 30 at first and second spaced-apart positions 40, 42. Positions 40, 42 are spaced apart by, for example, 8 mm, and define a relatively rigid tip segment 43 therebetween. It is expected that positions 40, 42 can be spaced apart by other distances, such as from 3 mm to 80 mm, depending on the construction of tip portion 30, the procedure to be accomplished, and other factors. In the embodiment of FIG. 2, position 42 is at the distal end 34 of catheter body 24; however, other positions are also possible.

Catheter body 24 is coupled to first manipulator 12, manipulator wires 26, 28 are coupled to second and third manipulators 14, 16, and sheath 22 is coupled to fourth manipulator 18. Manipulator wires 26, 28 are flexible but are sufficiently stiff and have sufficient columnar strength so that they can apply significant pushing forces against tip portion 30 at positions 40, 42. Manipulator wires 26, 28 are designed to position tip segment 43 at a variety of orientations; the orientation of tip segment 43, as will be discussed below, in large part determines the orientation of tip portion 30. The stiffness and columnar strength of manipulator wires 26, 28 will depend on the amount of force desired to be exerted by tip portion 30, the flexibility or stiffness of the tip portion, the size of tip portion 30, and other such considerations.

Manipulator wires 26, 28 are preferably made with sufficiently large diameters so as not to injure cardiac or other organ tissue when the wire is pressed against the tissue. Also, wires 26, 28 can have a tissue-protecting coating to help prevent tissue injury.

Wires 26, 28 can be made with circular or flattened cross-sectional shapes. Circular cross-sectional manipulator wires preferably have diameters of about 0.51–0.89 mm (0.020–0.035 inch); manipulator wires with flattened cross-sectional shapes are preferably at least about 0.51–0.89 mm (0.020–0.035 inch) thick by 0.51–2.5 mm (0.020–0.100 inch) wide. In one embodiment, each wire 26, 28 is a round wire made of a polymer-covered stainless steel wire and has an outside diameter of about 0.64 mm (0.025 inch).

Figure 3A:
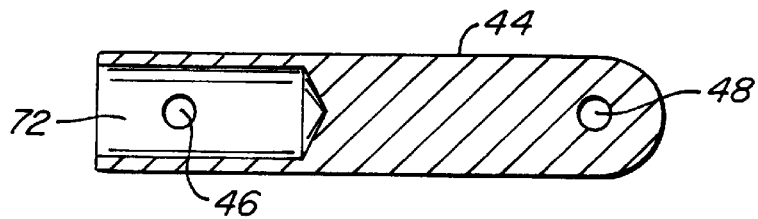
FIG. 3A is a simplified and enlarged cross-sectional view of the metal tip to be used with the tip portion of FIG. 3.
Figure 3:
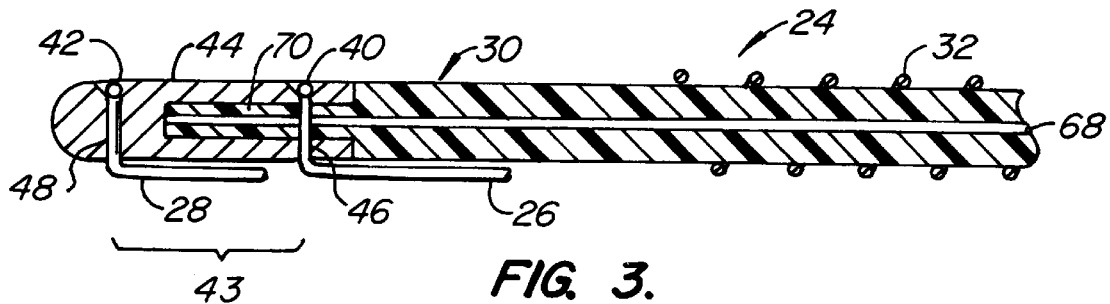
FIG. 3 is a simplified partial cross-sectional view of the distal end of the tip portion of the catheter body of FIG. 2.

FIG. 3 illustrates the distal end of the tip portion of the catheter body of FIG. 2. Tip portion 30 includes a tip 44, see FIG. 3A, typically made of stainless steel, having a pair of bores 46 formed through the tip. Manipulator wires 26, 28 are passed through bores 46, 48 and are secured within the bores so that manipulator wires 26, 28 can push or pull on tip portion 30 of catheter body 24a while permitting tip 44 to rotate freely about the axes of bores 46, 48.

Figure 3B:
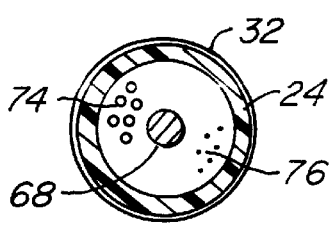
FIGS. 3B and 3C are simplified cross-sectional views of the tip portion of FIG. 3 illustrating a round core wire and a flattened core wire, respectively.
Figure 3C:
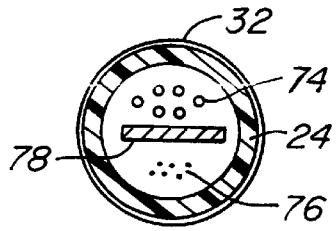

FIGS. 3B and 3C show the internal construction of tip portion 30 of FIG. 3 in cross-section. In FIG. 3B, the central lumen of tip section 30 houses a corewire 68 which is attached at its distal end to an adhesive 70 (see FIG. 3) within a central bore 72 (see FIG. 3A) and at its proximal end to first manipulator 12. Corewire 68 is pulled or pushed to cause tip portion 30 to bow out or to straighten. Electrical wires 74 and thermocouple wires 76 are also shown in FIGS. 3B and 3C.

It can be appreciated that the round corewire 68 shown in FIG. 3B can be replaced with flattened corewire 78 shown in FIG. 3C. Flattened corewire 78 imparts lateral rigidity to tip portion 30 in the transverse direction to its bending axis. This can improve stability, maneuverability, and contact force for tip portion 30.

Figure 4:
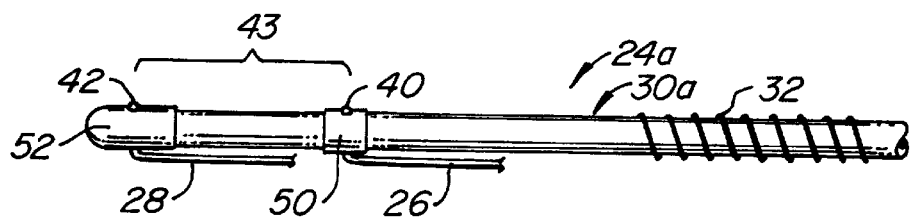
FIGS. 4–6 are three alternative embodiments of tip portions of FIG. 3.

FIG. 4 illustrates the distal end of the tip portion 30a of a catheter body 24a similar to the embodiment of FIG. 3. Instead of metal tip 44, the tip portion comprises a pair of metal keepers 50, 52, typically clasps or rings, at positions 40, 42.

Figure 5:
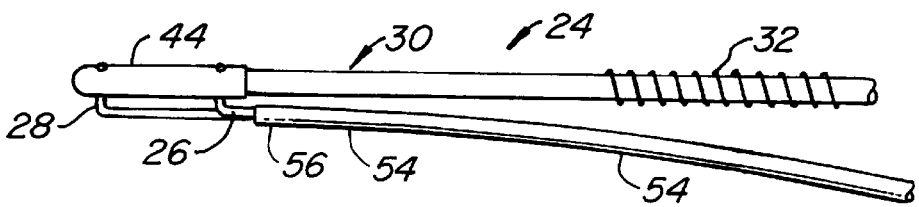

FIG. 5 is a modification of the embodiment shown in FIG. 3 in which a hypotube 54 is used to house manipulator wires 26, 28. The distal end 56 of hypotube 54 is open to permit manipulator wire 26, 28 to enter the hypotube. The use of hypotube 54 helps reduce friction and minimizes irritation and trauma to tissue during the insertion of catheter body 24 and the manipulation of manipulator wires 26, 28. Hypotube 54, which may or may not be axially manipulatable, also helps to control the manipulator wires to keep them from separating from one another too far proximally. Hypotube 54 can be made from a variety of materials including stainless steel and polymers.

Figure 6:
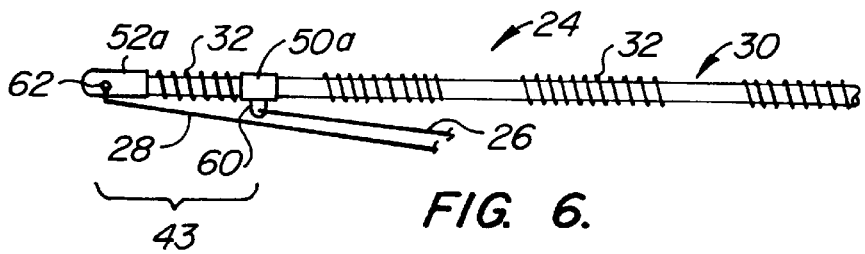

FIG. 6 illustrates an embodiment similar to that of FIG. 4. However, keeper 50a has an extension 60 to which manipulator wire 26 is secured. Keeper 52a has a through-hole 62 through which manipulator wire 28 passes. The embodiments of FIGS. 3 and 4 are generally preferred over the embodiment of FIG. 6 because of the lower profile of tip segment 43. Also, an electrode 32 is mounted along tip segment 43 as well as along the entire length of tip portion 30 proximal of the tip segment.

In the preferred embodiments, the electrodes 32 are spaced-apart from the tip 44 and keepers 50, 52. However, under appropriate condition, it may be desired to make tip 44 and one or both of keepers 50, 52 serve dual purposes, that is serve as attachment points 40, 42 for manipulator wires 26, 28 and as electrodes. In the preferred embodiments, the manipulator wires are solid; one of the manipulator wires, such as manipulator wire 26, could be replaced by a flexible tube or sheath 22 through which the other manipulator wire passes. Also, the connections between manipulator wires 26, 28 and tip portion 30 can take other forms, such as an axle connection or a living hinge made of, for example, a polymer material or a superelastic material such as nitinol.

Figure 7:
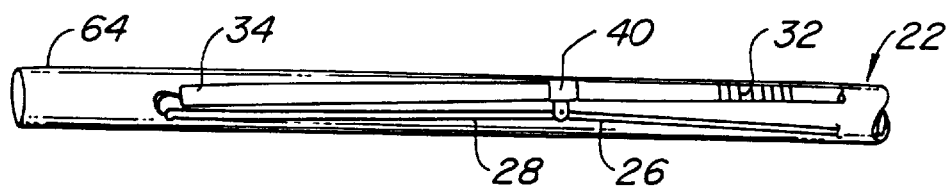
FIG. 7 illustrates the tip portion of an alternative embodiment of the invention housed within the distal end of the sheath.
Figure 7A:
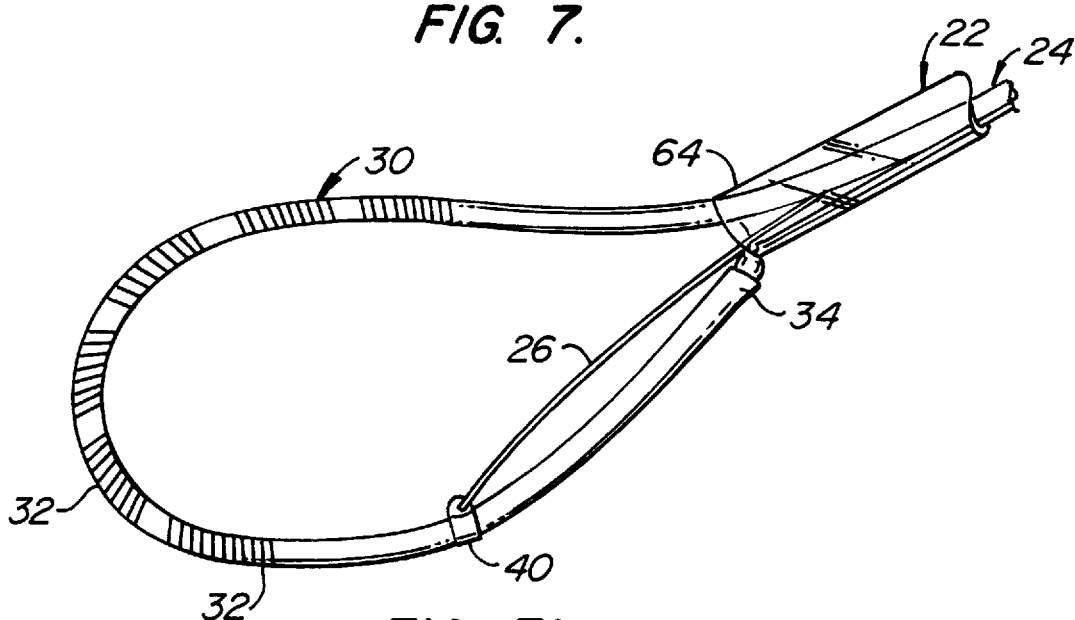
FIGS. 7A and 7B are plan and side views of the tip portion of FIG. 7 after the sheath has been pulled proximally to expose the distal end of the catheter body and the catheter body has been pushed through the distal end of the sheath.
Figure 7B:
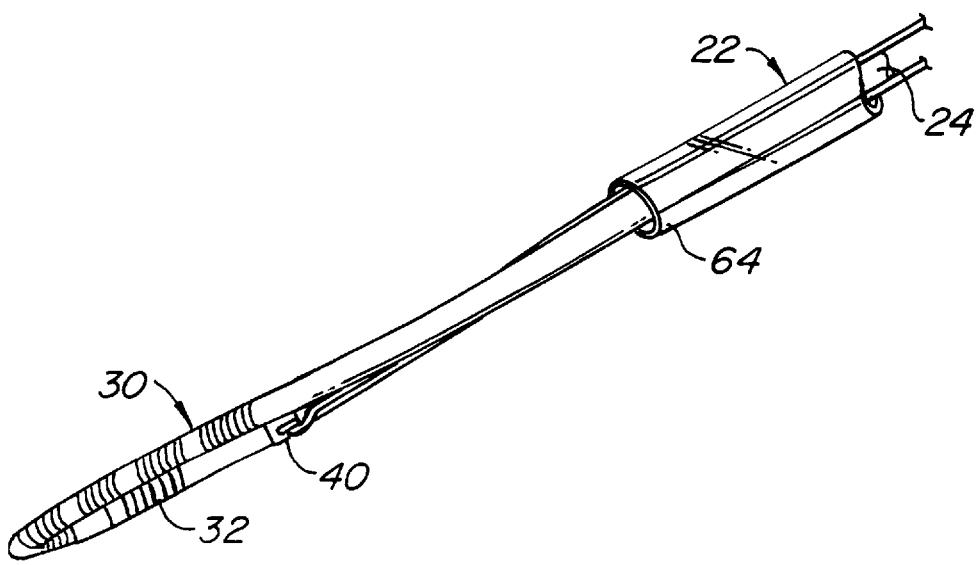

The use of catheter assembly 2 is described with reference to its use within a chamber of the heart. It could, however, be used in other situations as well. Typically, tip portion 30 of catheter body 24 is initially housed within sheath 20 adjacent to the distal end 64 of the sheath. See FIG. 7. Distal end 64 of sheath 22, with tip portion 30 of catheter body 24 housed therein, is transluminally positioned through a blood vessel so that distal end 64 is positioned within the heart. Once at the desired position, sheath 22 is pulled proximally using fourth manipulator 18 to expose distal end 34 of catheter body 24. Tip portion 30 assumes the in-plane orientation of FIGS. 7A and 7B by pulling sheath 22 back just far enough to expose distal end 34 and then pushing catheter body 24 distally while maintaining wire 28 fixed relative to sheath 22 and permitting proximal manipulator wire 26 to move freely. Tip portion 30 assumes the orientation of FIG. 2 from the orientation of FIG. 7 in the same basic manner; the main difference is that sheath 22 is pulled back further to expose more of tip portion 30 than with the orientation of FIG. 7A.

Figure 8A:
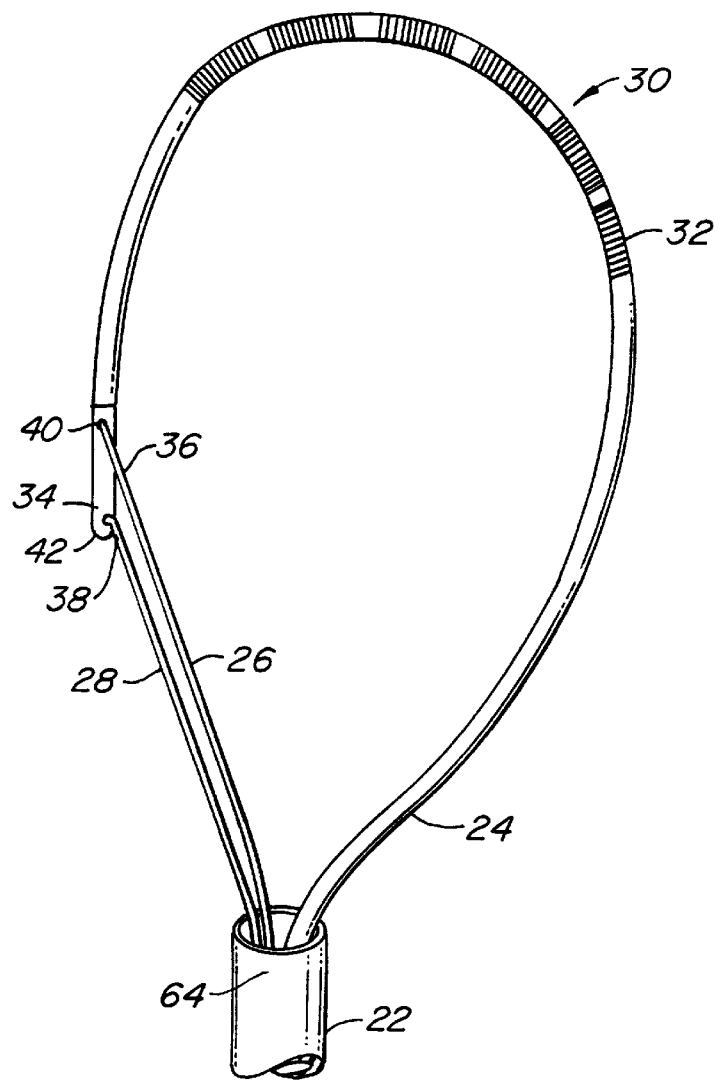
FIGS. 8A–8D illustrate a range of in-plane and substantially in-plane deflections of the tip portion of the catheter of FIG. 2 created by changing the orientation of the tip segment from generally perpendicular to the sheath axis in FIG. 8A to generally parallel to the sheath axis in FIG. 8D.

In-plane deflection (also called in-plane radial deflection), such as from the orientation of FIG. 2 to the orientation of FIG. 8A, is typically accomplished by pushing or advancing proximal manipulator wire 26 while maintaining distal manipulator wire 28 in position causing tip portion 30 to bow generally upwardly. This causes tip segment 43 to be close to being parallel to sheath axis 66 and permits electrodes 32 to make a lesion on the roof of the atrium generally aligned with axis 66 of sheath 22.

Figure 8D:
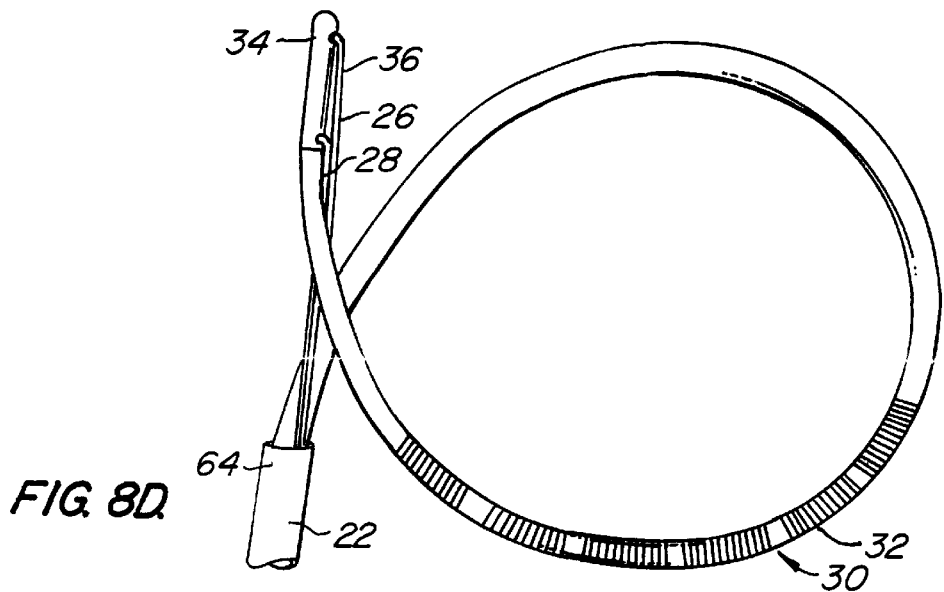
Figure 8B:
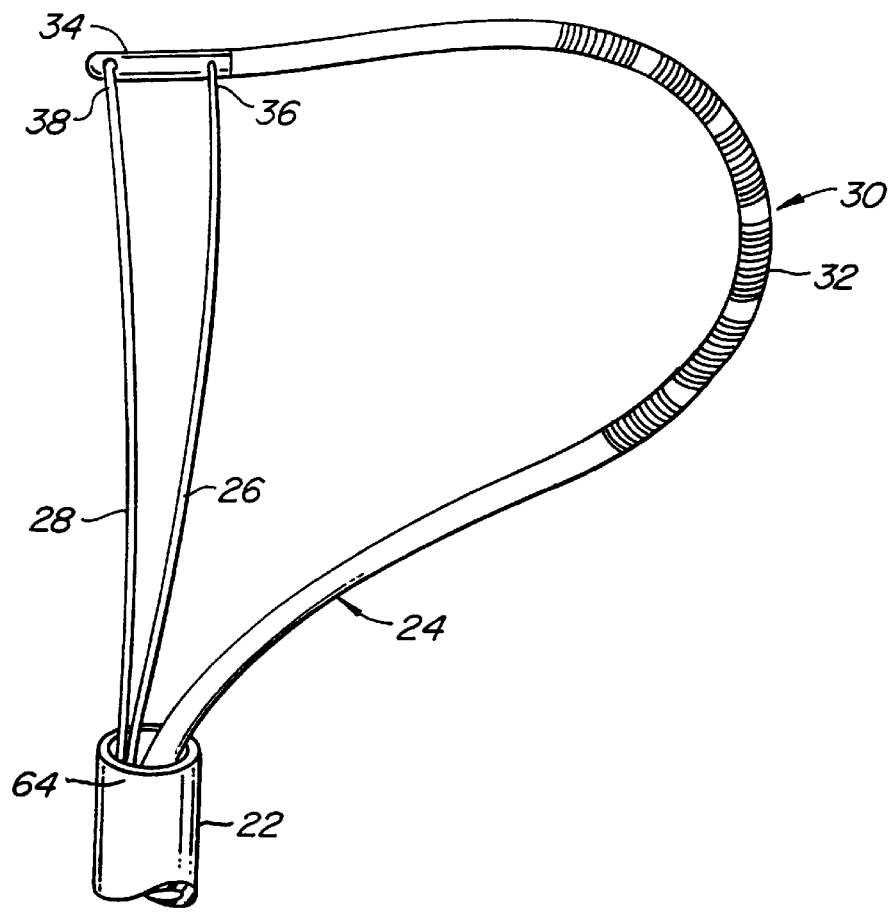

Tip portion 30 is moved from the orientation of FIG. 8A to the orientation of FIG. 8B by pulling back on second manipulator 14, thus pulling proximal wire 26 back in a proximal direction, while pushing on fourth manipulation, thus pushing sheath 22 distally, while maintaining manipulators 12, 16, in position to deflect tip segment 43 to an orientation generally perpendicular to the axis 66 of sheath 22. Manipulator wires 26, 28 are stiff enough and have sufficient columnar strength to effectively push or pull on tip portion 30 at positions 40, 42. The orientation of FIG. 8B permits electrodes 32 to create a lateral lesion. The stability of tip portion 30 is much greater, compared with the use of a single manipulator wire in conventional bowing catheters, due to the use of manipulator wires 26, 28. Also, the amount of radial deflection possible (see FIGS. 2 and 8B) is also greater with the use of wires 26, 28.

Figure 8C:
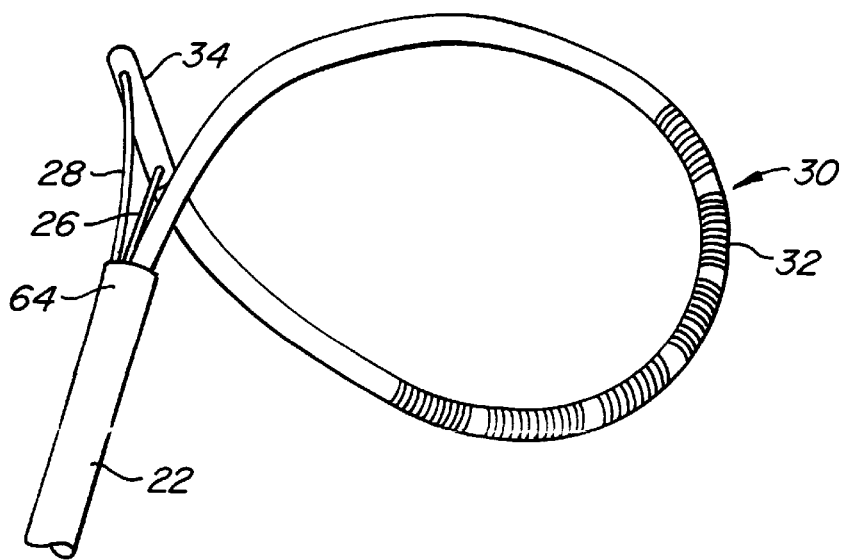

Tip portion 30 shown in FIG. 8C illustrates the tip portion in a complete loop. Tip segment 43 has moved from the position of FIG. 8B to the position of FIG. 8C by pulling on proximal manipulator wire 26 until position 42 is distal of position 40 but before tip segment 43 is parallel to axis 66. This orientation positions electrodes 30 both laterally and proximally. FIG. 8D illustrates a continuation of the movement of tip portion 30 of FIG. 8C wherein distal manipulator wire 28 has been pushed distally until tip segment 43 is generally parallel to axis 66. Doing so orients electrodes 32 in a proximal orientation to permit ablation along lines adjacent the entry of sheath 22 into the chamber. The movement of tip portion 30 to the orientations of FIGS. 8C and 8D is considered substantially in-plane deflection.

Figure 9:
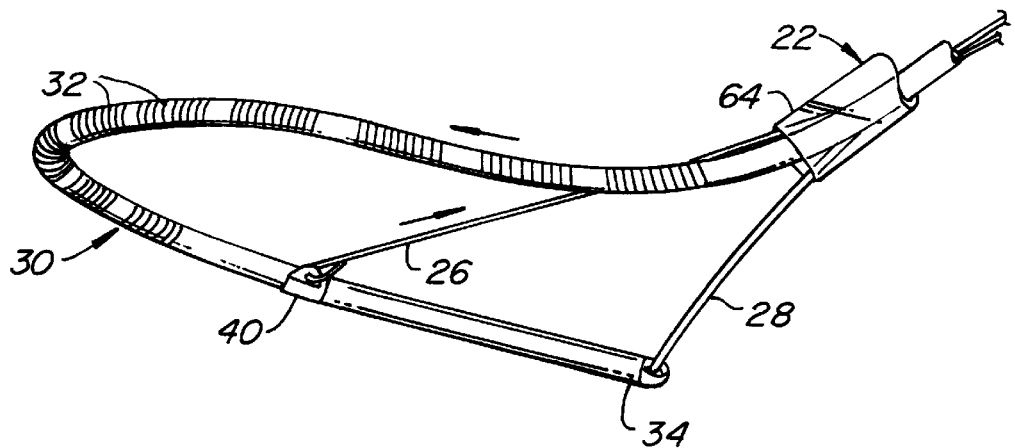
FIGS. 9 and 9A, 10 and 10A, 11 and 11A show pairs of views of successive out-of-plane deflections of the tip portion of FIG. 7 after the first manipulator wire has been pulled, the catheter shaft has been pushed and the distal end of the tip portion has remained at the same position within the heart.
Figure 9A:
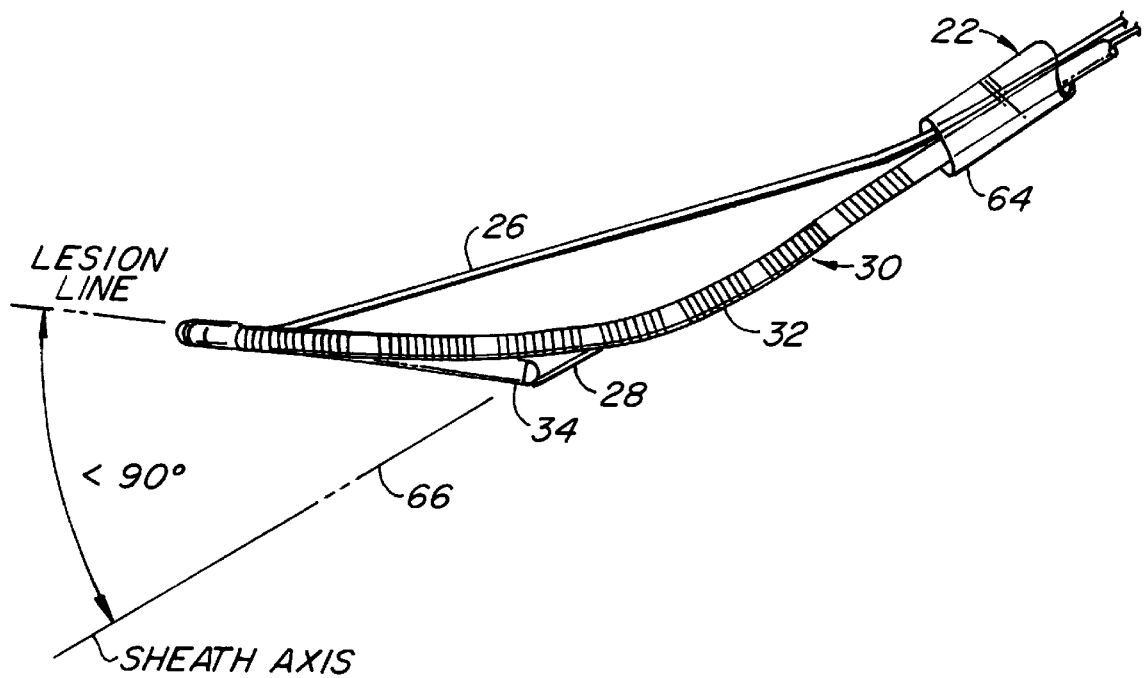
Figure 10:
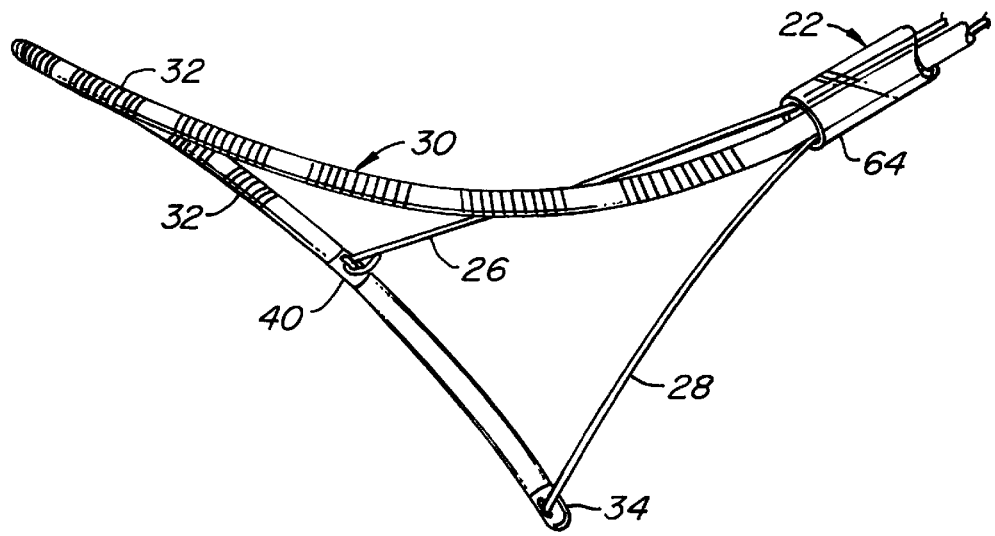
Figure 10A:
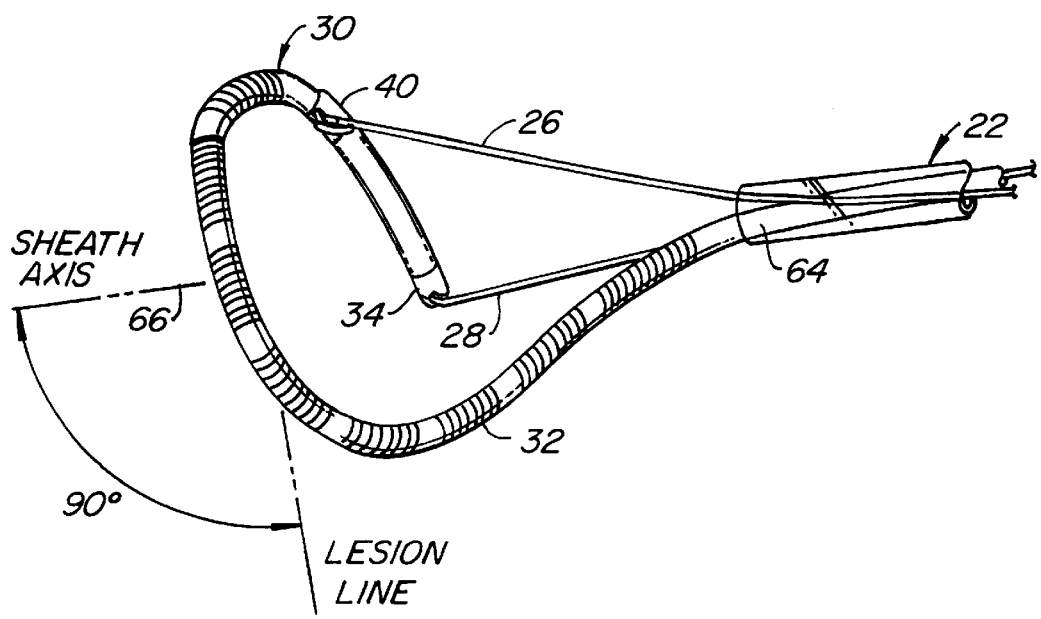
Figure 11:
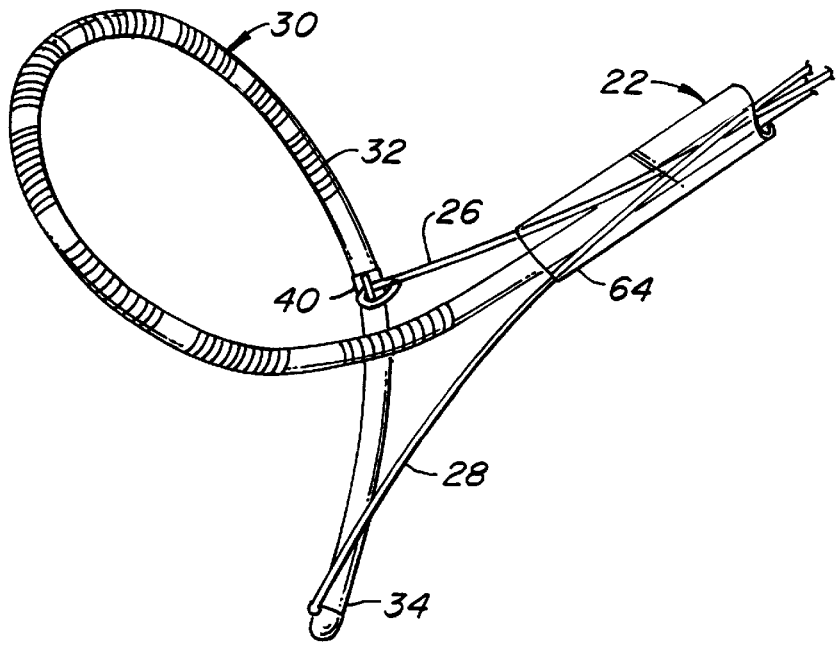
Figure 11A:
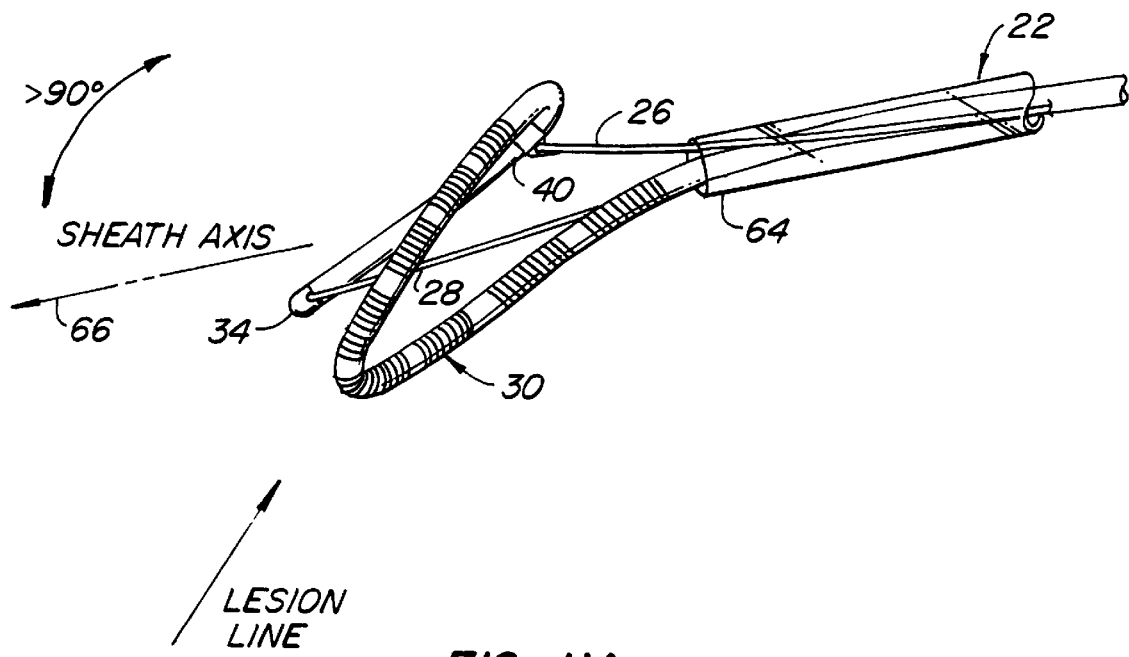

Out-of-plane deflection of tip portion 30 when starting from the general orientation of FIG. 2 is shown in FIGS. 9, 9A and can proceed as follows. Manipulator wire 26 is pulled proximally, while catheter body 24 is pushed distally, preferably while maintaining distal end 34 of catheter body 24 at a fixed position within the heart. Doing so causes tip portion 30 to bend out of the original plane of FIG. 2 to the out-of-plane (three-dimensional) configuration illustrated in FIGS. 9, 9A. FIGS. 10 and 10A, 11 and 11A illustrate further orientations resulting from the continued movement of wire 26 and catheter body 24. The lesion lines which can be created can vary over a wide range of angles as indicated in FIGS. 9A, 10A and 11A.

The amount of out-of-plane deflection is preferably at least about 90° in one lateral direction, and more preferably at least about 180° in one lateral direction.

Figure 12:
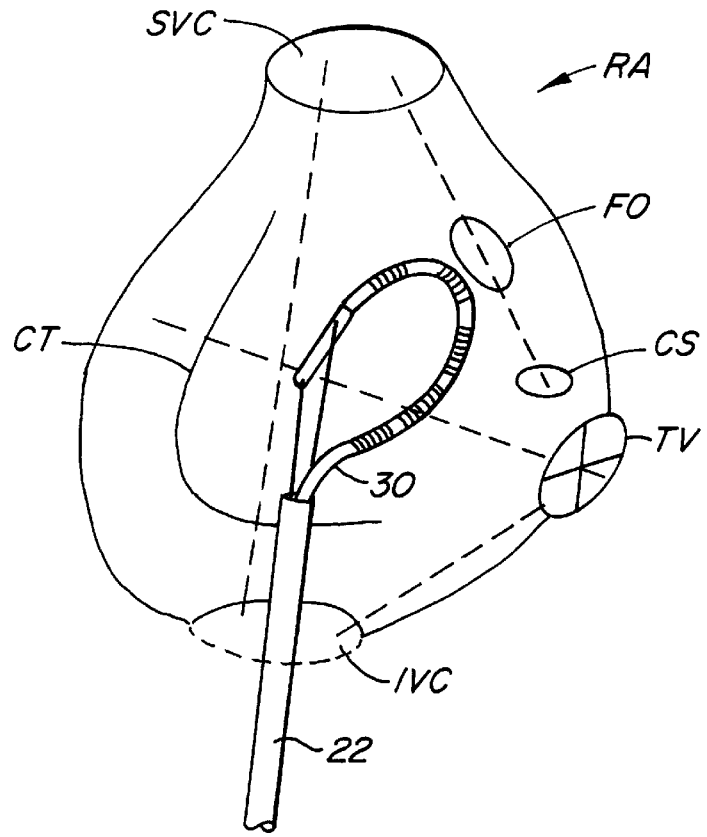
FIGS. 12 and 13 are simplified views of the right atrium and the left atrium of a heart illustrating various sites important in the treatment of atrial fibrillation and atrial flutter and showing introduction of the distal portion of the catheter of FIG. 1 therein.

FIG. 12 illustrates, in schematic form, a right atrium RA having a superior vena cava SVC, an interior vena cava IVC, a tricuspid valve TV, a coronary sinus CS, and fossa ovalis FO. Also shown is the crista terminalis, a ridge on the internal surface of the right atrium. The distal end of a catheter assembly is seen passing through the IVC whereupon tip portion 30 can be manipulated into a variety of in-plane and out-of-plane configurations to ablate tissue, typically along paths connecting two or more of the indicated structures.

Figure 13:
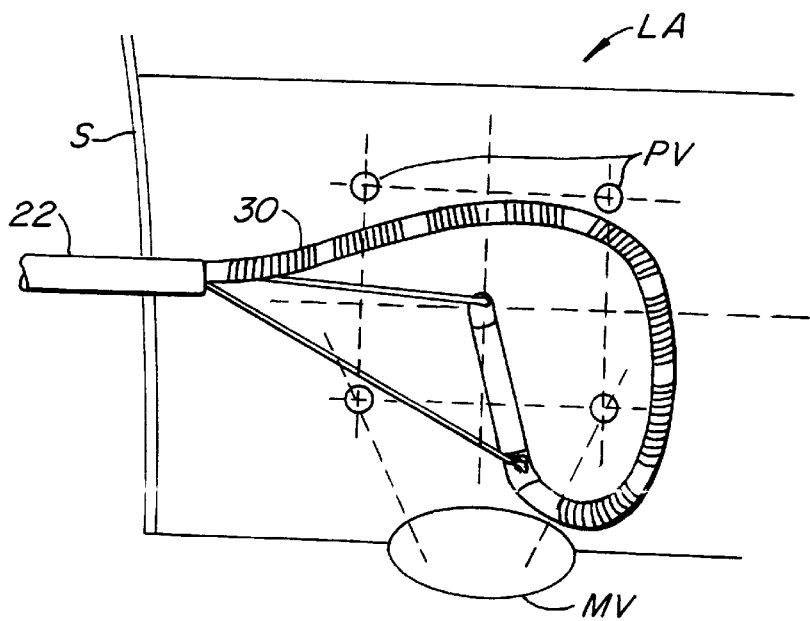

FIG. 13 illustrates, in schematic form, the passage of distal end 64 of sheath 22 through the septum 8 of the left atrium LA for ablating tissue between and among various sites, including pulmonary veins PV and a mitral valve MV. Typical lesion lines are indicated by dashed lines in FIGS. 12 and 13.

The methods of manipulating tip portion 30 into the various shapes shown in the figures can be varied from those described. It is preferred, however, that manipulations be conducted in such a manner that only one manipulator 12–18 need be moved at any one time while the remaining manipulators can be left to move freely relative to housing 10 or can be secured relative to one or more of the various components of assembly 2. In some situations it may be desired to use more than two manipulator wires.

Other different types of manipulations can be performed, including rotating or torquing tip portion 30 by, for example, torquing one or both of manipulator wires 26, 28 or by rotating the entire proximal end assembly 4. The stability created by the use of elements 26, 28 helps maintain such laterial deflection in-plane when desired.

The amount of force which can be exerted by tip portion 30 against the surface is typically at a maximum when tip portion 30 is generally aligned with sheath axis 66 as illustrated in FIGS. 2 and 8A. In one example, a catheter without manipulator wires 26, 28 in an orientation similar to that of FIG. 2 could exert a maximum force on the chamber wall of only about 0.8 oz.; the same catheter with manipulator wires 26, 28 mounted to positions 40, 42 about 8 mm apart permitted a force of about 6.5 oz. to be exerted against the chamber wall. When the lesion site is not in the direction of sheath axis 66, the amount of force which can be exerted by tip portion 30 will typically be lower, but the ratio of the amount of force exertable with and without manipulator wires 26, 28 is expected to be greater than in the example above.

Figure 14:
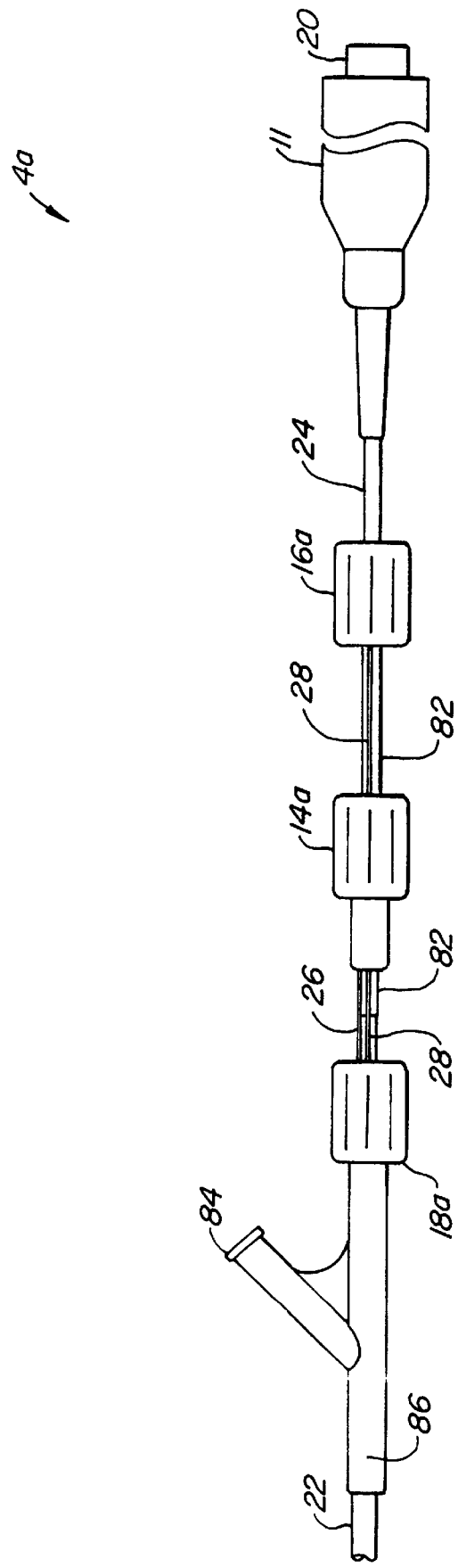
FIG. 14 illustrates an alternative embodiment of the proximal end assembly of FIG. 1.

FIG. 14 illustrates an alternative embodiment of proximal end assembly 4 of FIG. 1. Assembly 4a does not use a basic housing 10 as in the embodiment of FIG. 1. Rather, housing 10 is replaced by a housing/manipulator 11 from which shaft 24 extends. Housing/manipulator 11 and shaft 24 are connected to one another so that shaft 24 is moved by moving housing/manipulator 11. Instead of the manipulators 14, 16 and 18 of the FIG. 1 embodiment, proximal end assembly 4a uses three Touhy-Borst-type connectors as manipulators 14a, 16a, 18a; manipulators 14a, 16a, 18a have radially inwardly compressible O-rings which permit the manipulators to be secured into place. Manipulator 16a is mounted over shaft 24 so that manipulator 16a can be secured onto shaft 24. Distal manipulator wire 28 extends from manipulator 16a so that locking manipulator 16a onto shaft 24 locks distal wire 28 and shaft 24 together. A metal tube 82 extends distally from manipulator 16a and moves with manipulator 16a; manipulator shaft 24 passes through tube 82 while distal manipulator wire 28 extends along the outside of the tube. Manipulator 14a is mounted over distal manipulator wire 28 and metal tube 82 so that tightening manipulator 14a locks manipulator 14a to both distal wire 28 and tube 82. Proximal manipulator wire 26 is connected to and extends distally from an extension 83 of manipulator 14a. Thus, locking manipulator 14a onto distal wire 28 and tube 82 locks proximal and distal wires 26, 28 to one another. Finally, a sheath manipulator 18a, including a flush channel 84 extending from a body 86, is positioned distally of proximal manipulator 14a. Shaft 24 and proximal and distal manipulator wires 26, 28 pass through sheath manipulator 18a. Locking sheath manipulator 18a secures sheath 22 (extending from body 86), proximal and distal manipulator wires 26, 28 and shaft 24 (extending from the distal end of tube 82) to one another. Using the proximal end assembly 4a of FIG. 14 permits the physician to lock various components to one another, which is especially useful for one-handed operation and manipulation of the device. Other arrangements of manipulators and mechanisms for locking various components to one another could also be used.

The disclosures of each of the patents and applications referred to are incorporated by reference.

Other modifications and variations can be made through the disclosed embodiments without departing from the subject of the invention as defined in the following claims. For example, in some cases a manipulator may be the proximal end of a sheath, catheter body or manipulator wire.

What is claimed is:

1. A catheter assembly comprising:
   a proximal end assembly comprising first and second movable manipulators; and
   a catheter extending from the proximal end assembly, the catheter comprising:
      an elongate, flexible catheter body having a tip portion with an electrode mounted thereto; and
      first and second elongate push/pull manipulator elements having first and second distal ends, said first and second manipulator elements coupled to the first and second manipulators, said first and second distal ends connected to first and second spaced-apart positions along the tip portion, said first and second positions defining a tip segment therebetween;
   whereby manipulation of the first and second manipulators causes longitudinal movement of the first and second manipulator elements thereby deflecting the tip portion.

2. The catheter assembly according to claim 1, wherein said first and second manipulator elements each have sufficient strength to deflect said tip portion by pushing on the tip portion when axial movement is applied to at least one of the first and second manipulator elements by said first and second manipulators.

3. The catheter assembly according to claim 1, wherein the tip portion has a plurality of electrodes mounted thereto.

4. The catheter assembly according to claim 1, wherein the tip portion comprises a laterally-stabilized, substantially uni-directionally bending, flattened corewire.

5. The catheter assembly according to claim 1 wherein the tip portion comprises a corewire having a round cross-sectional shape.

6. The catheter assembly according to claim 1 wherein the tip portion has a distal end and the second manipulator element is coupled to the distal end of the tip portion.

7. The catheter assembly according to claim 1 wherein said first and second spaced-apart positions are separated by about 3 mm to 80 mm.

8. The catheter assembly according to claim 1 wherein the proximal end assembly comprises a housing and said manipulators are movably mounted to the housing.

9. The catheter assembly according to claim 8 wherein said manipulators are mounted to the housing for linear movement relative to the housing.

10. The catheter assembly according to claim 8 wherein said manipulators are securable at a continuous range of chosen positions relative to the housing.

11. The catheter assembly according to claim 1 wherein the proximal end assembly comprises a third manipulator and the catheter body is coupled to the third manipulator.

12. The catheter assembly according to claim 11 wherein said catheter comprises a catheter sheath at least substantially housing said catheter body and the manipulator elements.

13. The catheter assembly according to claim 12 wherein said proximal end assembly comprises a fourth movable manipulator and the sheath is coupled to the fourth manipulator.

14. The catheter assembly according to claim 13 wherein the proximal end assembly comprises a housing and the manipulators are movably mounted to the housing.

15. The catheter assembly according to claim 1 wherein said catheter comprises a catheter sheath at least substantially housing said catheter body and the manipulator elements.

16. The catheter assembly according to claim 15 wherein said proximal end assembly comprises a fourth movable manipulator and the sheath is coupled to the fourth manipulator.

17. The catheter assembly according to claim 16 wherein the third manipulator is selectively securable to the catheter body to permit the second manipulator element and the catheter body to be secured to one another.

18. The catheter assembly according to claim 16 wherein the second manipulator is selectively securable to the first manipulator element to permit the manipulator elements to be secured to one another.

19. The catheter assembly according to claim 16 wherein the fourth manipulator is selectively securable to the first and second manipulator elements and the catheter body to permit said sheath, manipulator elements and catheter body to be secured to one another.

20. The catheter assembly according to claim 1 wherein the manipulator elements comprise at least one manipulator wire.

21. The catheter assembly according to claim 1 wherein the manipulator elements comprise generally parallel manipulator elements.

22. The catheter assembly according to claim 1 wherein the tip segment is generally rigid.

23. The catheter assembly according to claim 1 further comprising an electrode mounted to the tip segment.

24. A method for positioning the tip portion of an electrophysiology catheter within a patient comprising the following steps:
   introducing the tip portion of an electrophysiology catheter body into a region of a patient;
   forming a radially-deflected bow in the tip portion; and
   deflecting the bowed tip portion by:
   manipulating first and second elongate manipulator elements connected to the tip portion at first and second spaced-apart positions, said first and second positions defining a tip segment therebetween.

25. The method according to claim 24 wherein said manipulating step comprises the step of pushing on the tip portion by at least one of the first and second manipulator elements.

26. The method according to claim 24 further comprising the step of selecting a catheter with the first and second spaced apart positions spaced apart by about 3 mm to 80 mm.

27. The method according to claim 24 further comprising the step of selecting a catheter with the second position at the distal end of tip portion.

28. The method according to claim 24 wherein the introducing step is carried out with the tip portion at least substantially housed within a hollow sheath.

29. The method according to claim 28 wherein the deflecting step causes the tip segment to move among orientations oriented between being generally parallel to and perpendicular to an axis extending from the hollow sheath.

30. The method according to claim 28 wherein the forming step comprises the steps of:

extending at least said tip segment from said hollow sheath; and restraining at least one of the first and second positions with at least one of the first and second manipulator elements.

31. The method according to claim 30 wherein said forming and deflecting steps are carried out using first, second, third and fourth manipulators, all movably mounted to a housing of a proximal end assembly, coupled to the first and second manipulator elements, the catheter body and the hollow sheath respectively.

32. The method according to claim 24 wherein the deflecting step comprises the step of laterally deflecting the bowed tip portion.

33. The method according to claim 32 wherein said laterally deflecting step is carried out to laterally deflect the bowed tip portion up to at least about 180°.

34. The method according to claim 24 wherein the deflecting step is carried out to cause out-of-plane, three-dimensional deflection of the bowed tip portion so that the bowed tip portion significantly changes its shape during such deflection.

35. The method according to claim 24 further comprising the step of selectively securing the second manipulator element to the catheter body.

36. The method according to claim 24 further comprising the step of selectively securing the manipulator elements to one another.

37. The method according to claim 24 further comprising the step of selectively securing the sheath, the manipulator elements and the catheter body to one another.

38. The method according to claim 24 further comprising the step of urging the bowed tip against a tissue surface of the patient with a contact force of up to at least about 30 gm.

39. A method for positioning the tip portion of an electrophysiology catheter within a patient comprising the following steps:

introducing the tip portion of an electrophysiology catheter body into a region of a patient;

forming a radially-deflected bow in the tip portion; and deflecting the bowed tip portion to cause out-of-plane, three-dimensional deflection of the bowed tip portion, the deflecting step is being carried out by manipulating first and second manipulator elements connected to first and second spaced-apart positions along the tip portion.

40. The method according to claim 39 further comprising the step of selecting a catheter with the first and second spaced apart positions spaced apart by about 3 mm to 80 mm.

41. The method according to claim 39 further comprising the step of selecting a catheter with the second position at the distal end of tip portion.

42. The method according to claim 39 wherein the introducing step is carried out with the tip portion at least substantially housed within a hollow sheath.

43. The method according to claim 42 wherein the forming step comprises the steps of:

extending at least a distal end of said tip portion from said hollow sheath; and restraining a part of the tip portion with at least one of said first and second manipulator elements.

44. The method according to claim 42 wherein said forming and deflecting steps are carried out using first, second, third and fourth manipulators, all movably mounted to a housing of a proximal end assembly, coupled to the first and second manipulator elements, the catheter body and the hollow sheath respectively.

45. The method according to claim 39 wherein said deflecting step is carried out to deflect the bowed tip portion up to at least about 180°.

46. The method according to claim 39 further comprising the step of urging the deflected bowed tip against a tissue surface of the patient with a contact force of up to at least about 30 gm.

47. The method according to claim 39 further comprising the step of selectively securing the second manipulator element to the catheter body.

48. The method according to claim 39 further comprising the step of selectively securing the manipulator elements to one another.

* * * * *